United States Patent
Selzer

(10) Patent No.: US 6,652,891 B2
(45) Date of Patent: Nov. 25, 2003

(54) CO-ENZYME Q10 DIETARY SUPPLEMENT

(75) Inventor: Jonathan Selzer, New Haven, CT (US)

(73) Assignee: HerbaSway Laboratories, LLC, Wallingford, CT (US)

( * ) Notice: Subject to any disclaimer, the term of this patent is extended or adjusted under 35 U.S.C. 154(b) by 105 days.

(21) Appl. No.: 10/015,420

(22) Filed: Dec. 12, 2001

(65) Prior Publication Data

US 2003/0113307 A1 Jun. 19, 2003

(51) Int. Cl.[7] .......................... A61K 35/78; A01N 65/00

(52) U.S. Cl. ....................... 424/757; 424/725; 424/773; 424/774; 424/777; 514/456; 514/458

(58) Field of Search ................................. 424/725, 773, 424/774, 777, 757; 514/458, 456

(56) References Cited

U.S. PATENT DOCUMENTS

| | | | |
|---|---|---|---|
| 4,084,010 A | | 4/1978 | Takemoto et al. |
| 4,827,062 A | * | 5/1989 | Saeki et al. .................. 514/690 |
| 5,626,868 A | | 5/1997 | Morancais et al. |
| 5,866,158 A | | 2/1999 | Ribier et al. |
| 6,045,826 A | | 4/2000 | Borowy-Borowski et al. |
| 6,124,442 A | | 9/2000 | Zhou et al. |
| 6,159,476 A | | 12/2000 | Djananov et al. |
| 6,161,172 A | | 12/2000 | Narayan et al. |
| 6,166,077 A | | 12/2000 | De Simone |
| 6,184,255 B1 | | 2/2001 | Mae et al. |
| 6,203,818 B1 | | 3/2001 | Vester |
| 6,232,346 B1 | | 5/2001 | Sole et al. |
| 6,245,378 B1 | | 6/2001 | Cavazza |
| 6,248,363 B1 | | 6/2001 | Patel et al. |
| 6,300,377 B1 | * | 10/2001 | Chopra ....................... 514/715 |
| 6,312,703 B1 | | 11/2001 | Orthoefer |
| 6,372,234 B1 | * | 4/2002 | Deckers et al. ............. 424/450 |
| 6,441,050 B1 | * | 8/2002 | Chopra ....................... 514/675 |

OTHER PUBLICATIONS

Computer Derwent Abs 1984–265–265868 JP59161313 Sep. 1984.*

Abrahamsson, K., Ericksson, B.O., Holme, E., Jodal, U., Jonsson, A., Lindstedt, S. Pivalic Acid–Induced Carnitine Deficiency and Physical Exercise in Humans. Metabolism: Clinical & Experimental, 45 (12): 1501–7, Dec. 1996.

Anand, I., Chandrashekhan, Y., De Giuli, F., Pasini, E., Mazzoletti, A., Confortini, R., Ferrari, R. Acute and Chronic Effects of Propionyl–L–Carnitine on the Hemodynamics, Exercise Capacity, and Hormones in Patients with Congestive Heart Failure. Cardiovascular Drugs & Therapy. 12 (3): 291–9, Jul. 1998.

Brass, E.P., Hiatt, W.R. The Role of Carnitine and Carnitine Supplementation During Exercise in Man and in Individuals with Special Needs. Journal of the American College of Nutrition, 17 (3) : 207–15, Jun. 1998.

Brevetti, G., Di Lisa, F., Perna, S., Menabo, R., Barbato, R., Martone, V.D., Siliprandi, N. Carnitine–Related Alterations in Patients with Intermittent Claudication: Indication for a Focused Carnitine Therapy, Circulation, 93 (9): 1685–9, May 1996.

Brevetti, G., Fanin, M., De Amicis, V., Carrozzo, R., Di Lello, F., Martone, V.D., Angelini, C. Changes in Skeletal Muscle Histology and Metabolism in Patients Undergoing Exercise Deconditioning: Effect of propionyl–L–carnitine. Muscle & Nerve, 20 (9) :1115–20, Sep. 1997.

Constantin–Teodosiu, D., Howell, S., Greenhaff, P.L. Carnitine Metabolism in Human Muscle Fiber Types During Submaximal Dynamic Exercise. Journal of Applied Physiology, 80 (3):1061–4, Mar. 1996.

Gleim, G.G., Glace, B. Carnitine as an Ergogenic Aid in Health and Disease [editorial; comment]. Journal of the American College of Nutrition, 17 (3): 203–4, Jun. 1998.

Heinonen, O.J. Carnitine and Physical Exercise. Sports Medicine, 22 (2): 109–32, Aug. 1996.

Kaikkonen, J., Kosonen, L., Nyyssonen, K., Porkkala–Sarataho, E., Salonen, R., Korpela, H., Salonen, J.T. Effect of Combined Coenzyme Q10 and d–alpha–tocopheryl Acetate Supplementation on Exercise–Induced Lipid Peroxidation and Muscular Damage: A Placebo–Controlled Double–Blind Study in Marathon Runners.. Free Radical Research, 29 (1): 85–92, Jul. 1998.

Lee, PJ, Harrison, EL, Jones MG, Chalmers RA, Leonard JV, Whipp BJ, "Improvement in exercise tolerance in isovaleric acidaemia with L–carnitine therapy" Journal of Inherited Metabolic Disease. 21(2):136–140, Apr. 1998.

Sole, M.J., Jeejeebhoy, K.N., abstract, The Failing Heart as a Starved Organ: Role of Nutrition in Heart Failure, Mar. 1998, Ottawa, Canada.

Sole, M.J., Keith, M., Ball, A., Kurian, R., Jeejeebhoy, K.N. Cardiovascular Pharmacology (The Failing Myocardium is Nutritionally Deficient). Journal of Cardiac Failure vol. 5 No. 3 Suppl. Sep. 1, 1999.

Sole, M.J., presentation slides, Heart Failure Society of America, 2.sup.nd Annual Meeting, Boca Raton, Florida, "The Fifth Paradigm: A New Look at Heart Failure", Sep. 1998.

Svesson, M., Malm C., Tonkonogi, M., Ekblom, B., Sjodin, B., Sahlin, K. Effect of Q10 Supplementation on Tissue Q10 Levels and Adenine Nucleotide Catabolism During High–Intensity Exercise. International Journal of Sport Nutrition, 9 (2): 166–80, Jun. 1990.

(List continued on next page.)

Primary Examiner—Herbert J. Lilling
(74) Attorney, Agent, or Firm—Carmody & Torrance LLP

(57) ABSTRACT

A liquid dietary supplement useful in increasing bodily levels of coenzyme Q10 is disclosed. The supplement comprises an oil in water emulsion of coenzyme Q10. The dietary supplement disclosed is pleasant tasting, is effectively absorbed into the body and is believed to provide substantial therapeutic effects.

8 Claims, No Drawings

OTHER PUBLICATIONS

Thompson, C.H., Irish, A.B., Kemp, G.J., Taylor, D.J., Radda, G.K. The Effect of Propionyl–L–carnitine on Skeletal Muscle Metabolism in Renal Failure. Clinical Nephrology, 47 (6) :372–8, Jun. 1997.

Vasankari, T.J., Kujala, U.M., Vasankari, T.M., Vuorimaa, T., Ahotupa, M. Increased Serum and Low–Density–Lipoprotein Antioxidant Potential After Antioxidant Supplementation in Endurance Athletes. American Journal of Clinical Nutrition, 65 (4) :1052–6, Apr. 1997.

Vukovich, M.D., Sharp, R.L., Kesl, L.D., Schaulis, D.L., King D.S. Effects of a Low–Dose Amino Acid Supplement on Adaptations to Cycling Training and Untrained Individuals. International Journal of Sport Nutrition, 7 (4): 298–309, Dec. 1997.

Weber, C. et al., Effect of Dietary Coenzyme Q as an Antioxidant in Human Plasma, Molec. Aspects. Med., vol. 15 (Supplement), pp. s97–s102, Dec. 1994. Molec. Aspects Med., (1994) vol. 15 (Supplement), pp. S97–S102.

Weston, S.B., Zhou, S., Weatherby, R.P., Robson, S.J. Does Exogenous Coenzyme Q10 Affect Aerobic Capacity in Endurance Athletes?International Journal of Sport Nutrition, 7 (3): 197–206, Sep. 1997.

* cited by examiner

CO-ENZYME Q10 DIETARY SUPPLEMENT

FIELD OF THE INVENTION

The present invention relates to a method and composition for providing a Coenzyme Q10 product in liquid form as a dietary supplement and/or therapeutic supplement.

BACKGROUND OF THE INVENTION

The uses of coenzyme Q10 as a dietary supplement are manifold and well documented in the scientific literature. Also known as ubidecarenone, it is an antioxidant that plays a critical role in cellular mitochondrial generation of energy, stimulates the immune system, increases circulation and strengthens the cardiovascular system. Deficiencies in coenzyme Q10 have been linked to several debilitating diseases. Current research, and clinical trials around the world are substantiating these and further claims, including periodontal disease, diabetes, asthma, allergies and other respiratory diseases, mental and psychological diseases, cancer, Alzheimer's disease, multiple sclerosis, muscular dystrophy, male impotency and diabetes. It is also being used to reduce side effects of cancer chemotherapy and the treatment of degenerative heart diseases.

Coenzyme Q10 is a class of physiological substances occurring as component factors of the mitochondrial electron transfer system within the biological cell. Coenzyme Q10 acts directly as an electron carrier in oxidative phosphorylation reactions, through metabolic pathways, particularly aerobic pathways, to produce ATP and hence energy. It seems that the demand for coenzyme Q10 is increased in normal subjects in the state of physical fatigue and patients with cardiovascular disease, chronic debilitating disease or on prolonged pharmacotherapy. As a result it may be a sound therapeutic choice to administer coenzyme Q10 to patients suffering from such problems.

In order for coenzyme Q10 to provide its therapeutic effect, the concentration of coenzyme Q10 must increase within the patient's cells. As a result, absorption into the blood stream as well as into the cells themselves is critical. Since coenzyme Q10 is only very sparingly soluble in aqueous solutions, in its natural solid form it is not very soluble in the aqueous gastric juices.

The amount of coenzyme Q10 in the body drops with age. Although it is available in our diet through beef, eggs, fish and organ meats, our assimilation of coenzyme Q10 becomes more difficult with age. As a result, its use as a dietary supplement has increased dramatically in the last decade.

Coenzyme Q10 is not very stable and deteriorates at temperatures above 115° F. It is not water-soluble and is generally provided to the consumer in the form of a hard gelatin capsule containing between 30–60 mg of the powdered coenzyme Q10. Because of this, the absorption of the coenzyme Q10 is limited by the capsule itself and the powdered form of the product. Capsules must be dissolved by the digestive system before their contents can be released into the digestive tract for eventual absorption into the blood stream. If the active ingredients are difficult to get across the membranes into the blood vessels, the absorption will be reduced.

Coenzyme Q10 is a difficult to absorb substance. For this reason, most suppliers recommend that it be taken with fatty foods. However, as a general health recommendation this is not advisable. Advances have been made to improve its absorbability by milling the powder to a very find mesh. The smaller the particle size, the better the absorption.

Thus, it is the object of this invention to provide the consumer with coenzyme Q10 in a novel liquid form, including the oils which have been found to be required for optimal absorption.

SUMMARY OF THE INVENTION

The inventors herein propose a novel liquid composition comprising coenzyme Q10 which optimizes its absorption into the blood stream and into the cells. Thus the novel composition provides an improved therapeutic effect over prior compositions.

The inventors have discovered that a specific oil in water emulsion comprising coenzyme Q10 accomplishes the foregoing objectives. The invention comprises adding coenzyme Q10 to the oil phase of an emulsion. Both the oil and water phases of the emulsion are supplemented with additional ingredients in order to optimize the effectiveness of the overall emulsion. This combination provides a coenzyme Q10 supplement with optimal absorption and therapeutic properties.

DETAILED DESCRIPTION OF THE INVENTION

The inventors herein propose a dietary supplement comprising an oil in water emulsion coenzyme Q10 supplement comprising an oil phase and a water phase wherein said oil phase comprises:

(a) vegetable oil;
(b) coenzyme Q10;
(c) optionally, but preferably, tocopherol or a tocopherol derivative (collectively tocopherol); and
(d) optionally, but preferably, an emulsifier;

and wherein said water phase comprises:

(a) water; and
(b) optionally, but preferably, at least one ingredient selected from the group consisting of extract of Lo Han, extract of Stevia, L-carnitine fumarate, Chinese licorice root extract, thickeners, gelling agents, stabilizing agents, glycerine, and mixtures of the foregoing.

The dietary supplement described herein requires a source of coenzyme Q10. Also known as ubidecarenone, coenzyme Q10 is typically depicted by the following chemical formula:

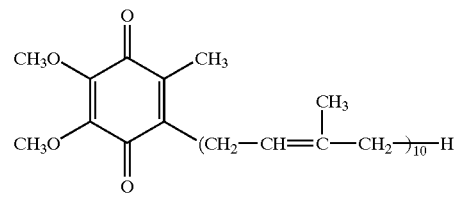

The inventors have found that a finely milled powder of coenzyme Q10, with average particle size from 49μ to 80μ is best for dissolving in the oil phase. The concentration of coenzyme Q10 in the dietary supplement can vary depending upon the desired dosage. For example, to provide 16.66 mg in a 1 ml serving, the coenzyme Q10 concentration should be about 1.49% by weight of the final product. Generally the concentration of coenzyme Q10 in the final product should preferably range from about 0.5 to 2.5 percent by weight.

The vegetable oil can be any oil derived from plants that is appropriate as a food additive such as soybean oil, sunflower foil, olive oil, corn oil and other similar plant (usually seed) derived oils generically referred to as vegetable oils. The concentration of vegetable oil in the dietary supplement can preferably range from about 2 to 25 percent by weight. Generally vegetable oils are considered mixtures of glycerides.

The dietary supplement also optionally but preferably comprises tocopherol or tocopherol derivatives. Tocopherols are a group of related isomers: alpha beta, gamma and delta tocopherol which together constitute vitamin E. The alpha form, $C_{29}H_{50}O_2$ (which occurs naturally as the d-isomer) is most potent biologically. All isomers are derivatives of dihydro-benzo-gamma-pyran, and differ from each other only in the number and position of the methyl groups. If used, the concentration of tocopherol in the dietary supplement preferably ranges from about 0.05 to 1.5 percent by weight.

The dietary supplement may also optionally but preferably comprise an emulsifier. The emulsifier can be any of a number of food grade products such as mon-and di-glycerides or lecithin (either egg or soy derived). The emulsifier should be one that is effective at achieving an oil in water emulsion. The inventors have found that lecithin is an effective emulsifier in this dietary supplement. Lecithin is generally a mixture of diglycerides of fatty acids linked to the choline ester of phosphoric acid. In particular the inventors have used Emulfluid™ as a preferred lecithin based emulsifier. Emulfluid™ is available from Lucas Meyer Company of Hamburg, Germany. If used, the concentration of emulsifier in the dietary supplement should preferably range from 0.025 to 1.5 percent by weight.

The vegetable oil, coenzyme Q10, and if use, the tocopherol and emulsifier, should be premixed together to form the oil phase of the dietary supplement. Once the oil phase is completely mixed, the water or water phase, which itself has been premixed is added to the oil phase. The combined oil and water phases are emulsified using a high shear mixer.

The water phase comprises water but will also preferably comprise at least one additive selected from the group consisting of extracts of the fruit of Lou Han, extracts of the leaves of stevia, L-carnitine fumarate, Chinese Licorice root, thickeners, gelling agents, stabilizing agents and combinations of the foregoing.

Lou Han Kuo (Lou Han) fruit comes from Momordica grosvenori also called Siraitia grosvenorii. Lou Han fruit is native to the People's Republic of China and Japan and is an edible fruit having an intensely sweet taste. It is reputed to possess healing properties for lung congestion, colds, sore throats, digestive and urinary disturbances, as well as antibiotic and antiseptic properties. Extracts of both fresh and dried Lou Han are available throughout the world and can be readily purchased. One suitable extract is available from the Shaanxi Youthsun Company located in China.

Various methods are known for preparing extracts of the Lou Han fruit and other natural sources. One such method is described in U.S. Pat. No. 6,124,442, wherein the starting plant source material is fresh plant material, for example cut pieces of freshly harvested Lou Han fruit. The fresh plant pieces are extracted by soaking in a bath of heated water, alcohol (preferably ethanol) or both. The initial process is preferably carried out in hot, preferably boiling water. Extraction in the bath may be carried out several times, each time saving the resulting liquid. The resulting extract liquid is then filtered through a suitable filter, such as a 40-mesh stainless steel screen. The thus-obtained solid material can then be extracted again. It may be preferable for a particular process to carry out more or less extraction steps with different volumes of liquid being used for each boiling or extraction step. The liquid extract may then be concentrated before use. In this regard, U.S. Pat. Nos. 6,124,442 and 4,084,010 are incorporated herein by reference in their entirety.

Stevia rebaudiana (Stevia) is also a plant which is native to the People's Republic of China. Extracts from the leaves of Stevia are commonly known and have been used as a natural sweetener in Asia for many years. Studies have demonstrated that extracts from the leaves of Stevia can have a variety of beneficial therapeutic effects including antibiotic properties especially against *E.Coli*, vasodilatation properties especially in the kidney, anti-hypertensive effects, beneficial effects on pancreatic beta cells, and enhancing the secretion of insulin. Extracts from the leaves of Stevia are known and can be purchased for use in formulating the compositions described herein. These extracts can be prepared using the same or similar techniques used for preparing extracts for Lou Han. One suitable extract is available from the Shaanxi Youthsun Company located in China.

Flavor stabilizers, such as Chinese licorice (glycyrrhiza uralensis) root extract and/or L-carnitine fumarate may be added to preserve and enhance flavor. Extracts of Chinese licorice root are well known and can be prepared using the same or similar methods to producing Lou Han extracts. One suitable Chinese licorice extract is available from the Shaanxi Youthsun Company of China. If used, the concentration of stabilizers, such as Chinese licorice root extract, may preferably range from about 0.001 to 15 percent by weight of the dietary supplement.

Gelling agents or thickeners, such as xanthan gum or galactoarabinan may be added to improve the stability of the emulsion. Suitable thickeners of this type may be purchased from the Kelco Company of Chicago, Ill. If used, the concentration of gelling agents or thickeners may preferably range from about 0.5 to 10 percent by weight of the dietary supplement.

Other optional materials may be included in the composition of this invention. Vitamins, minerals or other herbal extracts may be added for particular purposes or effects. Sugars such as fructose may be added but are not recommended. Artificial sweeteners such as xylitol may also be added. Other flavoring agents may also be utilized. Glycerin has proven to be a beneficial additive.

In preparing the dietary supplement the oil and water phases are each separately mixed and then combined to form the emulsions using high shear mixing. It is recommended that the consumer of the product ingest three or more servings per day such that approximately 30–45 mg of coenzyme Q10 are ingested per day.

The compositions of this invention are further described in the following examples which should be taken as illustrative only and not limiting in any manner.

EXAMPLE 1

A liquid Coenzyme Q10 supplement was prepared as follows:

| Component | % by Weight |
| --- | --- |
| (A) Oil Phase | |
| a. Coenzyme Q10 | 1.5 |
| b. Safflower Oil | 5 |
| c. Emulfluid F30 | 0.05 |
| d. Tocopherol | 0.2 |
| (B) Water Phase | |
| a. Water | 52.43 |

-continued

| Component | % by Weight |
|---|---|
| b. Glycerin | 34.6 |
| c. Lo Han Extract | 1.35 |
| d. Stevia Extract | 1.35 |
| e. Chinese Licorice Extract | 0.2 |
| f. Flavor | 3.36 |

Mix oil phase 30 minutes until dissolved

Mix water phase 10 minutes until dissolved

Add water phase to oil phase and emulsify 10 minutes with high shear mixing

EXAMPLE 2

A liquid coenzyme Q10 supplement plus L-carnitine fumarate was prepared as follows:

| Component | % by Weight |
|---|---|
| (C) Oil Phase | |
| a. Coenzyme Q10 | 1.5 |
| b. Safflower Oil | 5 |
| c. Emulfluid F30 | 0.05 |
| d. Tocopherol | 0.2 |
| (D) Water Phase | |
| a. Water | 44.7 |
| b. L-carnitine fumarate | 7.73 |
| c. Glycerin | 34.6 |
| d. Lo Han Extract | 1.35 |
| e. Stevia Extract | 1.35 |
| f. Chinese Licorice | 0.2 |
| g. Flavor | 3.36 |

Mix oil phase 30 minutes until dissolved

Mix water phase 10 minutes until dissolved

Add water phase to oil phase and emulsify 10 minutes with high shear mixing

What is claimed is:

1. A composition useful as a dietary supplement which composition comprises an emulsion comprising an oil phase and a water phase wherein said oil phase comprises:

(a) vegetable oil;

(b) coenzyme Q10;

(c) an emulsifier; and wherein the water phase comprises water and at least one additive selected from the group consisting of aqueous or alcoholic extract of the fruit of Lou Han, aqeous or alcoholic extract of the leaves of Stevia, aqueous or alcoholic Chinese licorice root extract and combinations of the foregoing.

2. A composition according to claim 1 wherein the oil phase also comprises tocopherol.

3. A composition according to claim 1 wherein the water phase also comprises at least one additive selected from the group consisting of, L-carnitine fumarate, thickeners, gelling agents, flavor stabilizing agents, glycerine, and combinations of the foregoing.

4. A composition according to claim 1 wherein the concentration of coenzyme Q10 in the dietary supplement ranges from 0.5 to 10 percent by weight.

5. A composition according to claim 2 wherein the concentration of coenzyme Q10 in the dietary supplement ranges from 0.5 to 10 percent by weight.

6. A composition according to claim 3 wherein the concentration of coenzyme Q10 in the dietary supplement ranges from 0.5 to 10 percent by weight.

7. A composition according to claim 3 wherein the oil phase also comprises tocopherol.

8. A composition according to claim 6 wherein the oil phase also comprises tocopherol.

* * * * *